United States Patent [19]

Jonsson et al.

[11] 4,112,272

[45] Sep. 5, 1978

[54] VALVE AND SWITCH DEVICE FOR MEASURING PRESSURE OF LIQUIDS IN LIVING OBJECTS

[75] Inventors: Sven Erik Jonsson, Kungsängen; Olov Valter Ekström, Brottby, both of Sweden

[73] Assignee: Siemens Aktiengesellschaft, Berlin & Munich, Fed. Rep. of Germany

[21] Appl. No.: 808,703

[22] Filed: Jun. 21, 1977

Related U.S. Application Data

[63] Continuation of Ser. No. 744,833, Nov. 24, 1976, abandoned, which is a continuation of Ser. No. 607,862, Aug. 25, 1975, abandoned, which is a continuation of Ser. No. 439,618, Feb. 4, 1974, abandoned.

[51] Int. Cl.[2] .......................... H01H 9/06; A61B 5/02

[52] U.S. Cl. ........................ 200/61.58 R; 128/2.05 D; 137/554; 200/61.86

[58] Field of Search .................. 128/2.05 D; 335/206; 137/554; 200/61.58 R, 61.86

[56] References Cited

U.S. PATENT DOCUMENTS 2,600,324 6/1952 Rappaport .................. 128/2.05 D X 3,633,615 1/1972 Rhodes, Jr. .......................... 137/554

FOREIGN PATENT DOCUMENTS 2,146,456 3/1972 Fed. Rep. of Germany ........... 137/554

*Primary Examiner*—Kyle L. Howell

*Attorney, Agent, or Firm*—Hill, Gross, Simpson, Van Santen, Steadman, Chiara & Simpson

[57] ABSTRACT

A valve and switch device for measuring pressure of liquids in living objects comprises a pressure converter which is hydraulically connected with the liquid to be measured, and which transforms the pressure to be measured into electrical signals. It transmits the signals to a measuring device for indication and/or registration. This measuring device has an electro-mechanical switch and valve mechanism for switching off to automatic zero balance and automatic calibration. The main device has a switchable valve unit connected to the pressure converter for supplying alternately to the pressure converter, by the shifting of an operating member, the pressure to be measured, a zero pressure for zero balancing, and possibly a reference pressure for calibration. The invention is particularly characterized, in that the operating member is connected with an electrical operating device arranged at the valve unit and operating the switching device of the measuring device simultaneously with the switching of the valve unit in such manner that, for zero pressure, it reaches the switch indication "zero balance", and, for reference pressure, it reaches the switch indication "calibration".

2 Claims, 3 Drawing Figures

VALVE AND SWITCH DEVICE FOR MEASURING PRESSURE OF LIQUIDS IN LIVING OBJECTS

This is a continuation of application Ser. No. 744,833, filed Nov. 24, 1976, now abandoned, in turn a continuation of Ser. No. 607,862 filed Aug. 25, 1975, now abandoned, in turn a continuation of Ser. No. 439,618 filed Feb. 4, 1974, now abandoned.

This invention relates to a device for measuring pressure of liquids in living objects.

The invention refers more particularly to a device of this type comprising a pressure converter which is hydraulically connected with the liquid to be measured, and which transforms the pressure to be measured into electrical signals and transmits these signals to a measuring device for indication and/or registration. The measuring device has a switching device for switching off to automatic zero balance and automatic calibration. The main device also has a switchable valve unit connected to the pressure converter for supplying alternately to the pressure converter, by the shifting of an operating member, the pressure to be measured, a zero pressure for zero balancing, and possibly a reference pressure for calibration.

A device of this type is described in the specification DOS No. 2,163,967. In this known device, the measuring device stands mostly separated from the valve unit, often in an adjacent room. These known devices have drawbacks consisting in that the operator must initially bring the valve unit into corresponding positions for zero balance and the setting of the measuring device, and then must correspondingly actuate the electrical switching means of the measuring device. This work is quite complicated for a single person, particularly when the valve unit and the measuring device are located in separate rooms. Therefore, the work is mostly carried out by two persons.

An object of the present invention is to eliminate this drawback and to simplify the servicing of the device.

Other objects will become apparent in the course of the following specification.

In the accomplishment of the objectives of the present invention, it was found desirable to connect the operating member with an electrical operating device arranged at the valve unit and operating the switching means of the measuring device simultaneously with the switching of the valve unit in such manner that, for zero pressure, it reaches the switch indication "zero balance", and for reference pressure, it reaches the switch indication "calibration".

In an advantageous embodiment of the present invention, it is suggested that magnetically operable switches shall be used as the switching devices, and that the operating member shall have a rod magnet which actuates the switches in the switch positions "zero balance" and "calibration". This provides a high precision for the switching on and off of these switch locations with a small disturbance possibility.

According to a further embodiment of the present invention, the switching devices are cast in an insulating material. This avoids the possibility that even in case of a possible penetration of a physiological salt solution into the switching devices, there should be an undesired galvanic bridging of contacts, and thus, operational disturbances.

The invention will appear more clearly from the following detailed description when taken in connection with the accompanying drawing, showing, by way of example only, a preferred embodiment of the inventive idea.

Figure 1:
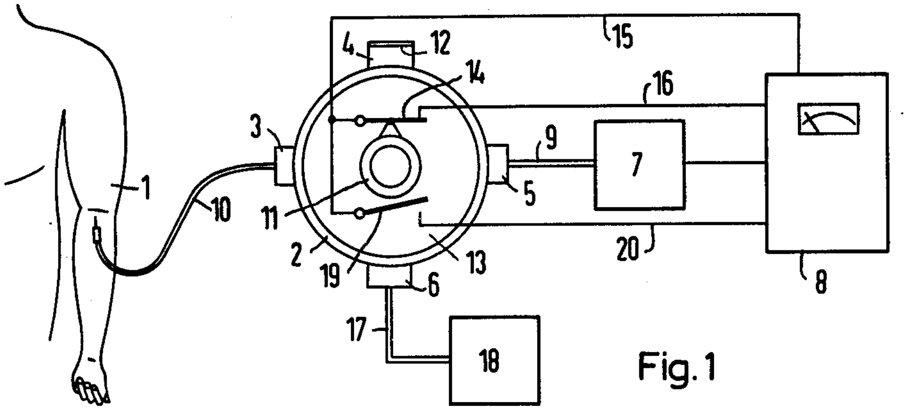
FIG. 1 is a diagrammatic side view of a blood-measuring device of the present invention.

FIG. 1 shows that the device for measuring blood pressure of a patient 1 consists of an axial valve unit 2 in which are formed four connections or ports 3 to 6, a mechanical-electrical pressure converter 7, and a measuring device 8. The valve unit 2, the connecting tubes 9 and 10 which connect the organic system of the patient 1 with the pressure converter 7, and a part of the pressure converter 7 are filled with a physiological salt solution, as is known in the art.

By operating an actuating member 11, located at the valve unit 2 and described later in detail in connection with FIG. 2, it is possible to provide a connection between the connecting member 5 and, one after the other, the connecting members 4, 3 and 6.

To avoid the indication of a wrong measuring value, a signal must be transmitted by the pressure converter 7 corresponding to zero pressure to the measuring device 8 for zero balance before the blood pressure measuring of the patient 1 can take place. For setting, a further signal must be transmitted which corresponds to the reference pressure. For that purpose, the actuating member 11 is rotated to provide a connection between the connecting member 4 and the connecting member 5, and thus a connection between the connecting member 4 and the pressure converter 7. The connecting member 4 is separated from the surrounding atmosphere only by the diaphragm 12. With that, an electrical signal is transmitted through the pressure converter 7 to the measuring device 8, which corresponds to atmospheric pressure and turns to zero pressure. At the same time, with the creation of the hyraulic connection, the electrical switching on of the measuring device takes place. For that purpose, the electrical switch 14, located in the axial switch casing 13, is also actuated by the actuating member 11. The switch 14 interconnects the lines 15 and 16, and thus switches over the measuring device 8 to automatic zero balance.

When the actuating member 11 is further turned to connecting member 6, the earlier hydraulic and electrical connection is interrupted, and a new connection between the connecting member 6 and the pressure converter 7 is provided. This connection extends over the connecting tube 17 with the reference pressure giver 18, which then supplies a reference pressure to the pressure converter 7. Thereupon, the pressure converter produces in a known manner an electrical signal of corresponding size which is transmitted to the measuring device 8. At the same time, the actuating member 11 actuates a second switch 19 located in the switch casing 13, which interconnects the conduits 15 and 20 and thus switches over the measuring device to automatic setting.

After the zero balancing and the setting of the measuring device 8 have been carried out in the described manner, a further turning of the actuating member 11 will connect the patient 1 with the connection 3 and the connecting tubes 9, 10 with the pressure converter 7, and then the blood pressure measuring can take place.

Figure 2:
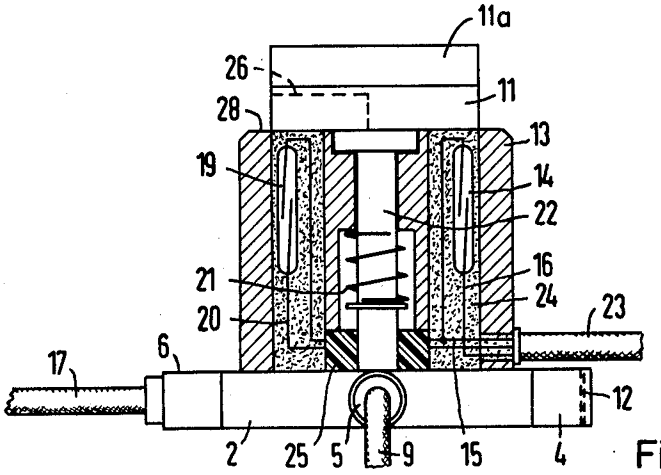
FIG. 2 is a transverse section through the actuating device.

FIG. 2 shows magnetically responsive encapsulated insulated switch contacts 14 and 19 in the switch casing 13 in radially angular spaced positions corresponding to the hydraulic connections 4 and 6 of the valve unit 2. The actuating member 11 is rotatably mounted upon the housing or casing 13 and includes a knob $11_a$ and a stem 22 extending through the casing 13. Conduits 15, 16 and 20, which are connected to the contacts 14 and 19 and lead to the measuring device 8, are combined in a cable 23. The two contacts 14 and 19, along with the parts of conduits 15, 16 and 20 located in the casing 13, are embedded in cast resin 24. The switch casing 13 is connected with the valve unit 2 by a rotary lock (not shown). A packing sleeve 25 is located between the casing 13 and the valve unit 2. The sleeve 25, jointly with the cast resin 24, prevents the penetration of the salt solution into the switch casing 13.

Figure 3:
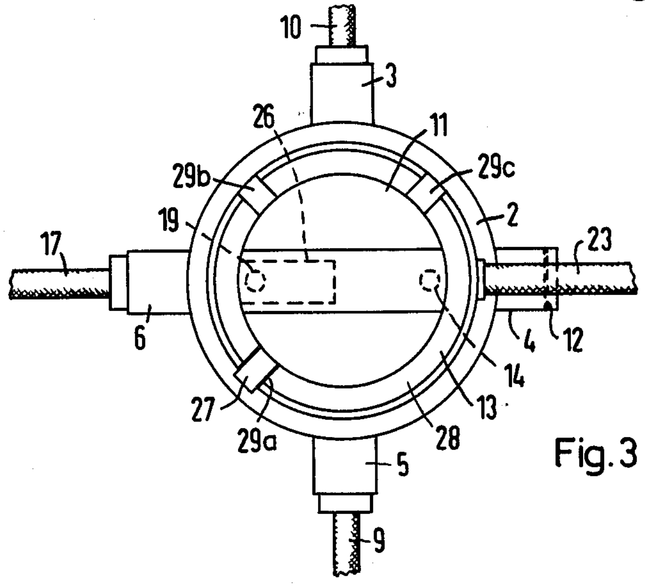
FIG. 3 is a top view of the actuating device.

FIG. 3 shows that a rod magnet 26 is located within the actuating member 11. As already stated, the actuating member 11 is a rotating part; it has a lug or slide piece 27, which is firmly connected and extends radially from its circumference. The slide piece 27 lies upon the front flat outer radial surface 28 of the switch casing 13, which is shaped as a sliding surface. In the position of the actuating member 11 shown in FIG. 2, the slide piece 27 extends at an angle of 45° to the rod magnet 26 and to the connections 3, 4 and 6. The front or outer surface 28 of the switch casing 13 is abuttingly engageable with a radial operating surface $11_b$ of the knob $11_a$ and has formed therein detents or recesses $29_a$, $29_b$ and $29_c$ receiving the lug or slide piece 27 which is biased toward the detents 29 by virtue of the force of the spring 21 (FIG. 2) under pressure upon the front surface 28 of the switch casing 13. When the slide piece 27 is inserted or received in any of the detents $29_a$, $29_b$ and $29_c$, the rod magnet 26 lies precisely in front of one of the connections or ports 3, 4 or 6. If, for example, the rod magnet 26 is located precisely in front of the connection 4, which is provided for the zero balancing of the measuring device 8, then the magnetic field will reach the switch contacts 14 and will actuate it. In that case, a corresponding electrical connection is produced between the valve unit 2 and the measuring device 8. As soon as the lug 27 formed on the knob $11_a$ of the actuating member 11 is raised from the recess $29_c$, the magnetic field between the rod magnet 26 and the switch 14 will be so lowered, due to the spacing, that the switch will be switched off again. When the actuating member is turned by 180°, the lug or slide piece 27 enters into the recess $29_a$, so that the rod magnet 26 will stand precisely in front of the switch 19 of the connection 6, which is connected by the connecting tube 17 with the reference pressure giver 18. As already stated, the switching on and off of the switch 19 takes place by the magnetic field of the rod magnet 26. The magnetic field is of such shape and strength that a connection is provided between the pressure converter 7 and the connections 4 and 6, which are switched on one after the other, before the switches 14 or 19 are switched on, and that they are switched off again before a new position is reached. This is of importance, since the signal produced by the pressure giver 7 must be supplied to the measuring device prior to the switch over into the corresponding switch position.

In order to measure the blood pressure of the patient 1, the knob $11_a$ of the actuating member 11 is rotated until the lug 27 is received in the detent $29_b$ and the rod magnet 26 stands precisely in front of or in registry with the connection 3. In this position of the actuating member 11, the patient 1 is connected with the pressure changer 7, and blood measuring takes place in the known manner. In this position, the magnet 26 has no function, since no switch is provided for the connection 3 and then in registry with the magnet 26.

What is claimed is:

1. An electro-mechanical switch and valve mechanism for use in a pressure measuring device comprising
   - an axial valve having a plurality of ports radially angularly arranged thereabout,
   - an electrical switch having an axial housing connected in fixed assembly to said valve and in axial alignment therewith,
   - a plurality of magnetically responsive encapsulated insulated switch contacts located within said switch housing in stationary relation thereto and in radially angularly spaced relation with respect to the axis thereof,
   - electrical conductors connected to said switch contact and extending through said switch housing,
   - a rotatable and axially shiftable actuating member having a knob disposed outside said switch housing and an axial stem means extending into switch housing and into said valve,
     - said stem means being operative to open and close said ports upon rotation thereof,
     - said knob having a radial operating surface,
     - said switch housing having a radial outer surface facing said operating surface and having disposed therewithin a spring member for biasing said operating surface axially into abutting engagement with said outer surface, and a magnet located in said knob for joint rotation therewith,
     - said operating surface and said outer surface having axially extending cooperating lug and detent means formed thereon including a lug and a plurality of radially angularly spaced detents for receiving said lug,
     - said knob being axially shiftable against the bias of said spring member to move said operating surface out of engagement with said outer surface and said lug out of said detents and then being rotatable to enable said lug to be selectively received in one of said detents and said operating surface to be shifted axially back into abutting engagement with said outer surface,
     - said magnet and said contacts being constructed and arranged so that said contacts operatively respond to said magnet only when said lug is received in one of said detents and said operating surface of said knob is shifted axially back into engagement with said outer surface of said switch housing.

2. The invention as defined in claim 1 wherein said lug is formed on said operating surface of said knob and said detents are formed in said outer surface of said switch housing.

* * * * *